United States Patent
Li et al.

(10) Patent No.: US 11,338,098 B2
(45) Date of Patent: May 24, 2022

(54) ELECTRONIC CIGARETTE, ATOMIZING ASSEMBLY, AND METHOD OF MANUFACTURING THE SAME

(71) Applicant: SHENZHEN SMOORE TECHNOLOGY LIMITED, Guangdong (CN)

(72) Inventors: Xiaoping Li, Guangdong (CN); Changyong Yi, Guangdong (CN)

(73) Assignee: SHENZHEN SMOORE TECHNOLOGY LIMITED, Shenzhen (CN)

( * ) Notice: Subject to any disclaimer, the term of this patent is extended or adjusted under 35 U.S.C. 154(b) by 272 days.

(21) Appl. No.: 16/568,566

(22) Filed: Sep. 12, 2019

(65) Prior Publication Data

US 2020/0086067 A1    Mar. 19, 2020

(30) Foreign Application Priority Data

Sep. 14, 2018  (CN) .......................... 201811076736.1

(51) Int. Cl.
*A24F 13/00* (2006.01)
*A24F 17/00* (2006.01)
(Continued)

(52) U.S. Cl.
CPC ................................. *A61M 11/042* (2014.02)

(58) Field of Classification Search
CPC ........ A24F 40/10; A24F 40/46; A61M 11/042
See application file for complete search history.

(56) References Cited

U.S. PATENT DOCUMENTS 10,791,762 B2 * 10/2020 Liu ........................ A24F 40/46
2015/0090280 A1 * 4/2015 Chen ...................... A61M 15/06
131/329
(Continued)

FOREIGN PATENT DOCUMENTS

WO     2015109476 A1    7/2015

OTHER PUBLICATIONS

Machine English translation of WO2015/109476A1.
Search Report issued in foreign counterpart European Application 19197171.2.

*Primary Examiner* — Abdullah A Riyami
*Assistant Examiner* — Thang H Nguyen
(74) *Attorney, Agent, or Firm* — Ladas & Parry LLP

(57) ABSTRACT

An electronic cigarette, an atomizing assembly, and a method of manufacturing an atomizing assembly. The atomizing assembly includes a liquid absorbing unit and a heating unit. The liquid absorbing unit is configured to absorb and store liquid and the liquid absorbing unit forms an atomizing channel therein and includes an atomizing surface on which the liquid is atomized and volatilized. The atomizing surface defines a boundary of the atomizing channel through which the smoke flows. The heating unit is configured to atomize the liquid and includes a buried portion and an embedded portion connected to each other. The embedded portion is embedded in the liquid absorbing unit and is internally tangent to the corresponding atomizing surface. The buried portion is wrapped in the liquid absorbing unit, wherein a predetermined distance is designed between the buried portion and the corresponding atomizing surface in a radial direction of the atomizing channel.

18 Claims, 13 Drawing Sheets

(51) Int. Cl.
*A24F 25/00* (2006.01)
*A61M 11/04* (2006.01)

(56) References Cited

U.S. PATENT DOCUMENTS

| | | | |
|---|---|---|---|
| 2015/0272218 A1* | 10/2015 | Chen | A61M 11/042 131/329 |
| 2018/0110940 A1* | 4/2018 | Suzuki | A24F 40/42 |
| 2019/0133186 A1* | 5/2019 | Fraser | A61M 15/06 |
| 2021/0084982 A1* | 3/2021 | Yilmaz | A61M 11/042 |

* cited by examiner

US 11,338,098 B2

ELECTRONIC CIGARETTE, ATOMIZING ASSEMBLY, AND METHOD OF MANUFACTURING THE SAME

CROSS-REFERENCE TO RELATED APPLICATION

This application claims the benefit of Chinese Patent Application No. 201811076736.1 filed on Sep. 14, 2018, the entire content of which is incorporated herein in its entirety.

TECHNICAL FIELD

The present disclosure relates to an electronic cigarette, an atomizing assembly, and a method of manufacturing an atomizing assembly.

BACKGROUND

Electronic cigarette is also known as virtual cigarette, electronic atomizer. As an alternative to cigarettes, electronic cigarettes are often used to quit cigarette. Electronic cigarettes have an appearance and similar taste to cigarettes, but generally do not contain tar, aerosols and other harmful ingredients in cigarettes.

Electronic cigarette is mainly composed of an atomizing assembly and a power source component. As the core device for generating atomizing gas by electronic cigarette, the atomizing effect thereof determines the quality and taste of the smoke. In general, the heating body of the atomizer is a spring-shaped heating wire, and the manufacturing process is to wind the linear heating wire around a liquid guide rope. Liquid in a liquid reservoir is adsorbed to the liquid guide rope through both ends of the liquid guide rope, and then heated and atomized by the heating wire. However, the liquid of this type electronic cigarette is completely absorbed by both ends of the liquid guide rope and then is atomized. Because an area of the end of the liquid guide rope is limited, liquid adsorption efficiency is low. Therefore, when a high-power heating wire is used, there will be insufficient liquid supply from the liquid guide rope, leading to dry burning and scorching smell.

In order to solve the problem of insufficient liquid supply, the improvement scheme in the prior art is to coat the spiral heating wire with a liquid guide structure such as a liquid guide cotton, in which the entire side surface of the liquid guide cotton can be used for liquid guide, so that the liquid supply amount is sufficient. However, it is still difficult to satisfy the requirement of the user in the improvement scheme.

SUMMARY

According to various embodiments of the present disclosure, an electronic cigarette, an atomizing assembly, and a method of manufacturing an atomizing assembly are provided.

An atomizing assembly includes a liquid absorbing unit and a heating unit. The liquid absorbing unit is configured to absorb and store liquid and the liquid absorbing unit forms an atomizing channel therein and includes an atomizing surface on which the liquid is atomized and volatilized. The atomizing surface defines a boundary of the atomizing channel through which the smoke flows. The heating unit is configured to atomize the liquid and includes a buried portion and an embedded portion connected to each other. The embedded portion is embedded in the liquid absorbing unit and is internally tangent to the corresponding atomizing surface. The buried portion is wrapped in the liquid absorbing unit, wherein a predetermined distance is designed between the buried portion and the corresponding atomizing surface in a radial direction of the atomizing channel.

An electronic cigarette includes the aforementioned atomizing assembly.

A method of manufacturing an atomizing assembly includes: providing a fixing post, defining a plurality of grooves circumferentially spaced apart on an outer circumferential surface of the fixing post, each groove extending in an axial direction of the fixing post, sleeving a spiral-shaped heating unit on the outer circumferential surface of the fixing post, an outer diameter of the fixing post being the same as an inner diameter of the spiral-shaped heating unit, placing the fixing post sleeved with the heating unit into a mold, injecting a first ceramic material into the grooves and onto a surface of the heating unit, and solidifying the first ceramic material by cooling, removing the fixing post from the solidified ceramic material, sintering the solidified ceramic material to form a liquid absorbing unit, wherein a part of the heating unit is embedded in the liquid absorbing unit and an edge of the heating unit is internally tangent to an inner surface of the liquid absorbing unit, and the other part of the heating unit being wrapped in the liquid absorbing unit.

A method of manufacturing an atomizing assembly includes: providing a fixing post, sleeving a spiral-shaped heating unit on an outer circumferential surface of the fixing post, a part of the heating unit being in contact with a part of corresponding outer circumferential surface, a predetermined distance being designed between the other part of the heating unit and the other part of corresponding outer circumferential surface in a radial direction of the fixing post, placing the fixing post sleeved with the heating unit into a mold, injecting a first ceramic material onto a surface of the heating unit, and solidifying the first ceramic material by cooling, removing the fixing post from the solidified ceramic material, sintering the solidified ceramic material to form a liquid absorbing unit, wherein a part of the heating unit is embedded in the liquid absorbing unit and an edge of the heating unit is internally tangent to an inner surface of the liquid absorbing unit, and the other part of the heating unit being wrapped in the liquid absorbing unit.

The details of one or more embodiments of the disclosure are set forth in the accompanying drawings and the description below. Other features, objects, and advantages of the disclosure will be apparent from the description and drawings, and from the claims.

BRIEF DESCRIPTION OF THE DRAWINGS

To illustrate the technical solutions according to the embodiments of the present disclosure or in the prior art more clearly, the accompanying drawings for describing the embodiments or the prior art are introduced briefly in the following. Apparently, the accompanying drawings in the following description are only some embodiments of the present disclosure, and persons of ordinary skill in the art can derive other drawings from the accompanying drawings without creative efforts.

DETAILED DESCRIPTION OF THE EMBODIMENTS

In order to facilitate understanding of the disclosure, the disclosure will be described more fully below with reference to the accompanying drawings. Preferred embodiments of the present disclosure are shown in the accompanying drawings. However, the present disclosure can be implemented in many different forms and is not limited to the embodiments described herein. On the contrary, it is an object of these embodiments to provide a more thorough understanding of the disclosure of the present disclosure.

It should be noted that when an element is referred to as being "fixed" to another element, it can be directly on the other element or it can also be presence of a central element. When an element is considered to be "connected" to another element, the element can be directly connected to the other element or it can be simultaneous presence of the central element. The terms "vertical", "horizontal", "left", "right" and the like used herein are for illustrative purposes only and are not meant to be the only embodiment.

Figure 1:
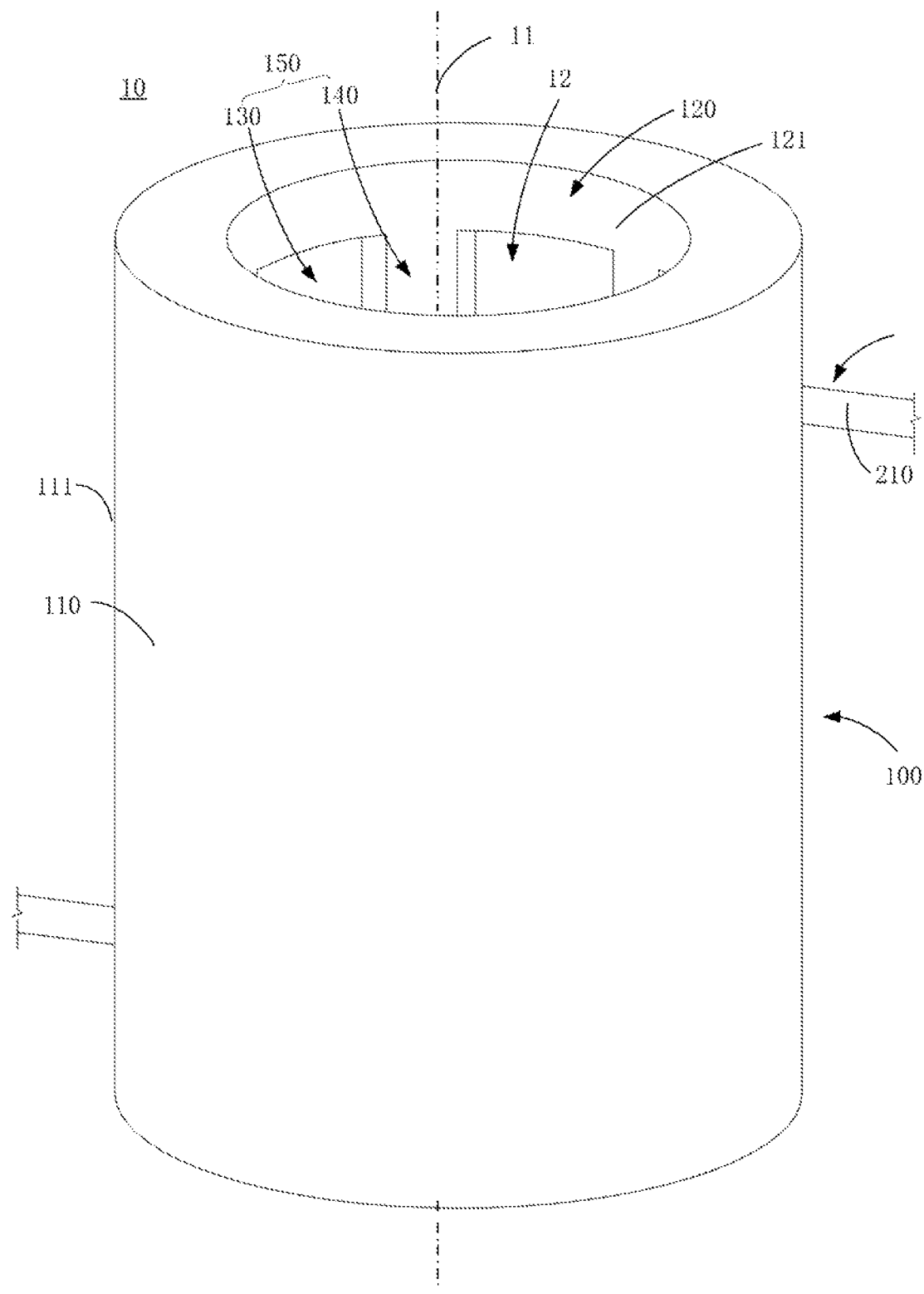
FIG. 1 is a perspective view of an atomizing assembly according to an embodiment.
Figure 2:
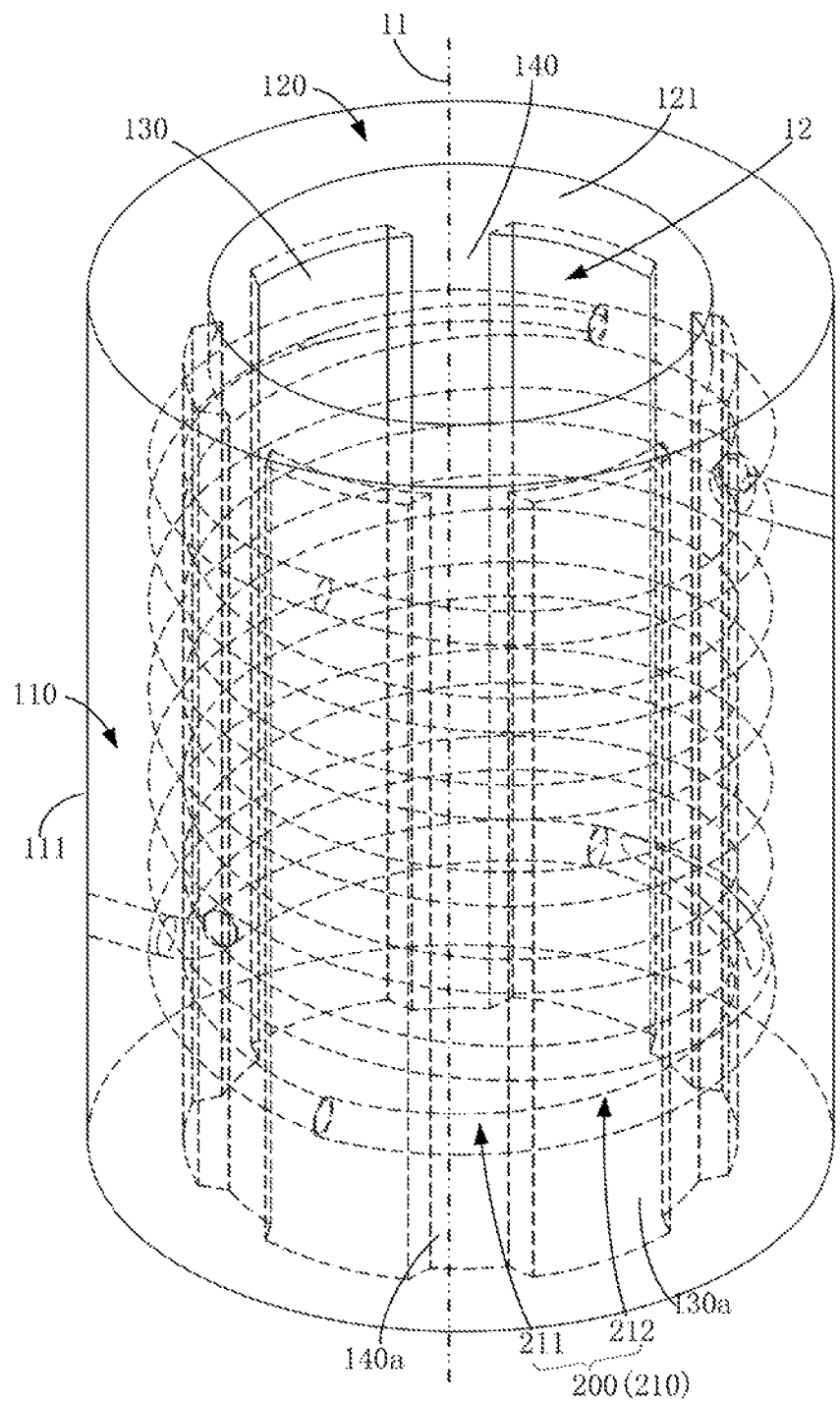
FIG. 2 illustrates an internal structure of the atomizing assembly of FIG. 1.
Figure 3:
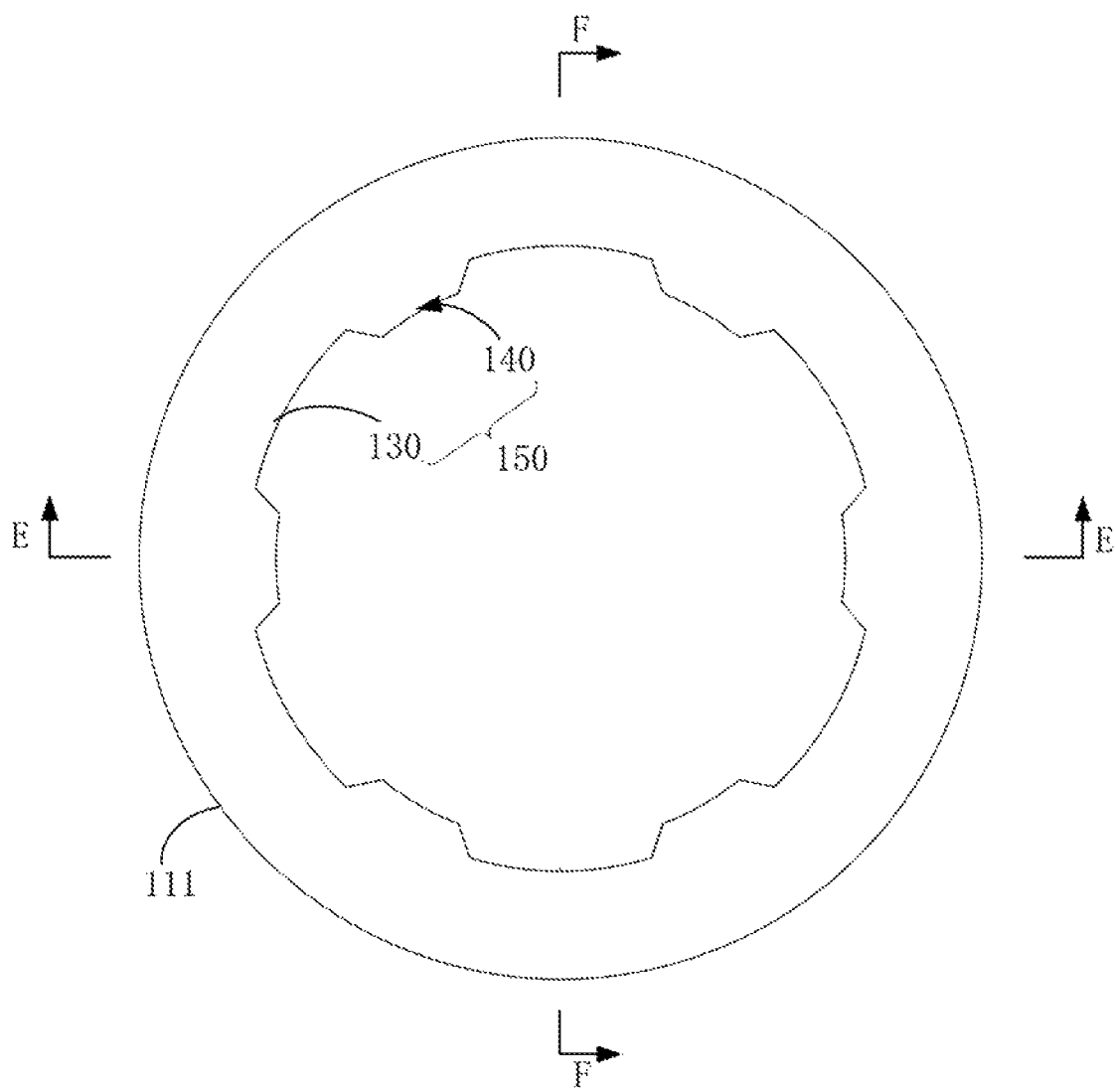
FIG. 3 is a bottom view of FIG. 1.
Figure 4:
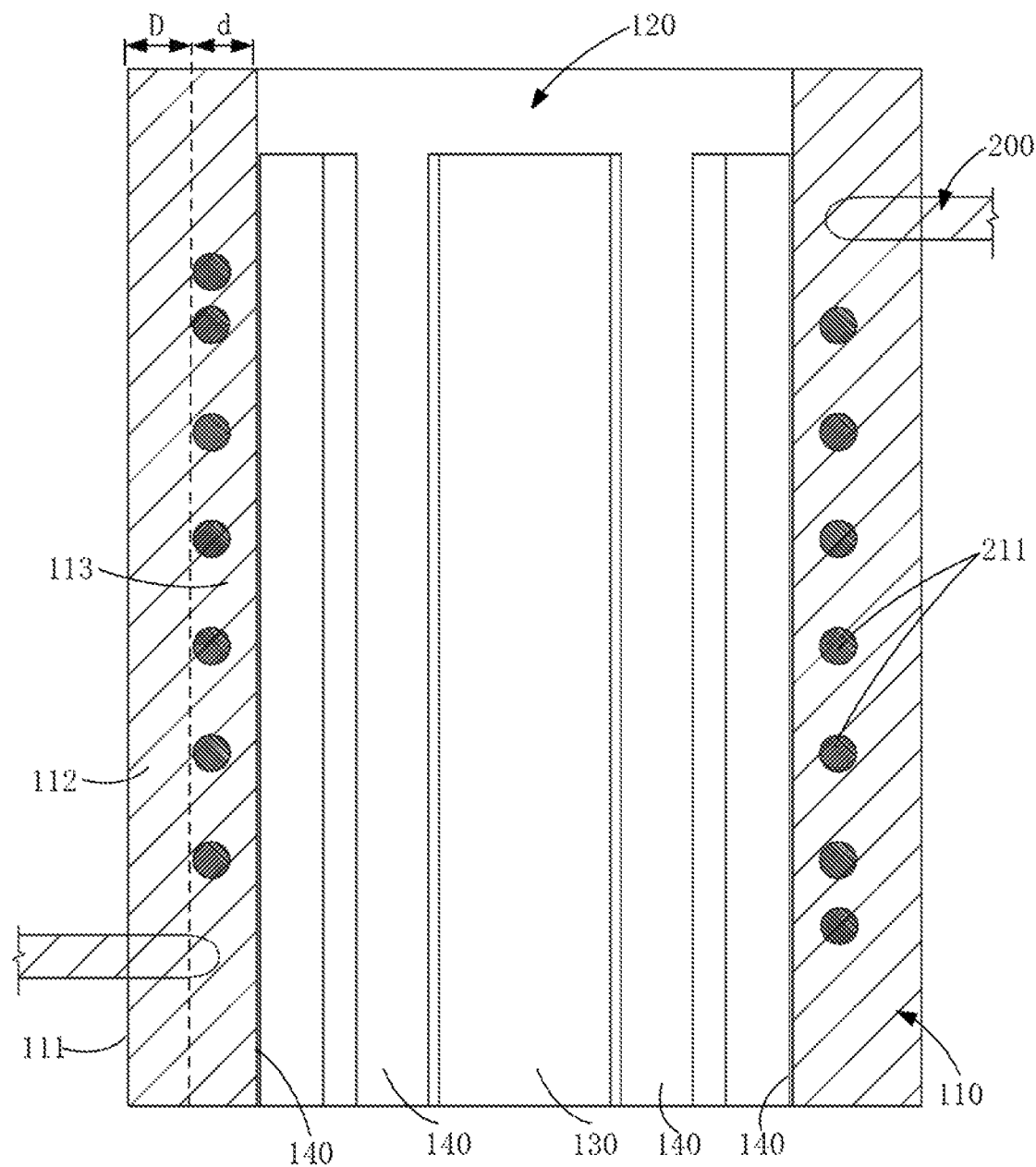
FIG. 4 is a cross-sectional view along the line E-E of FIG. 3.
Figure 5:
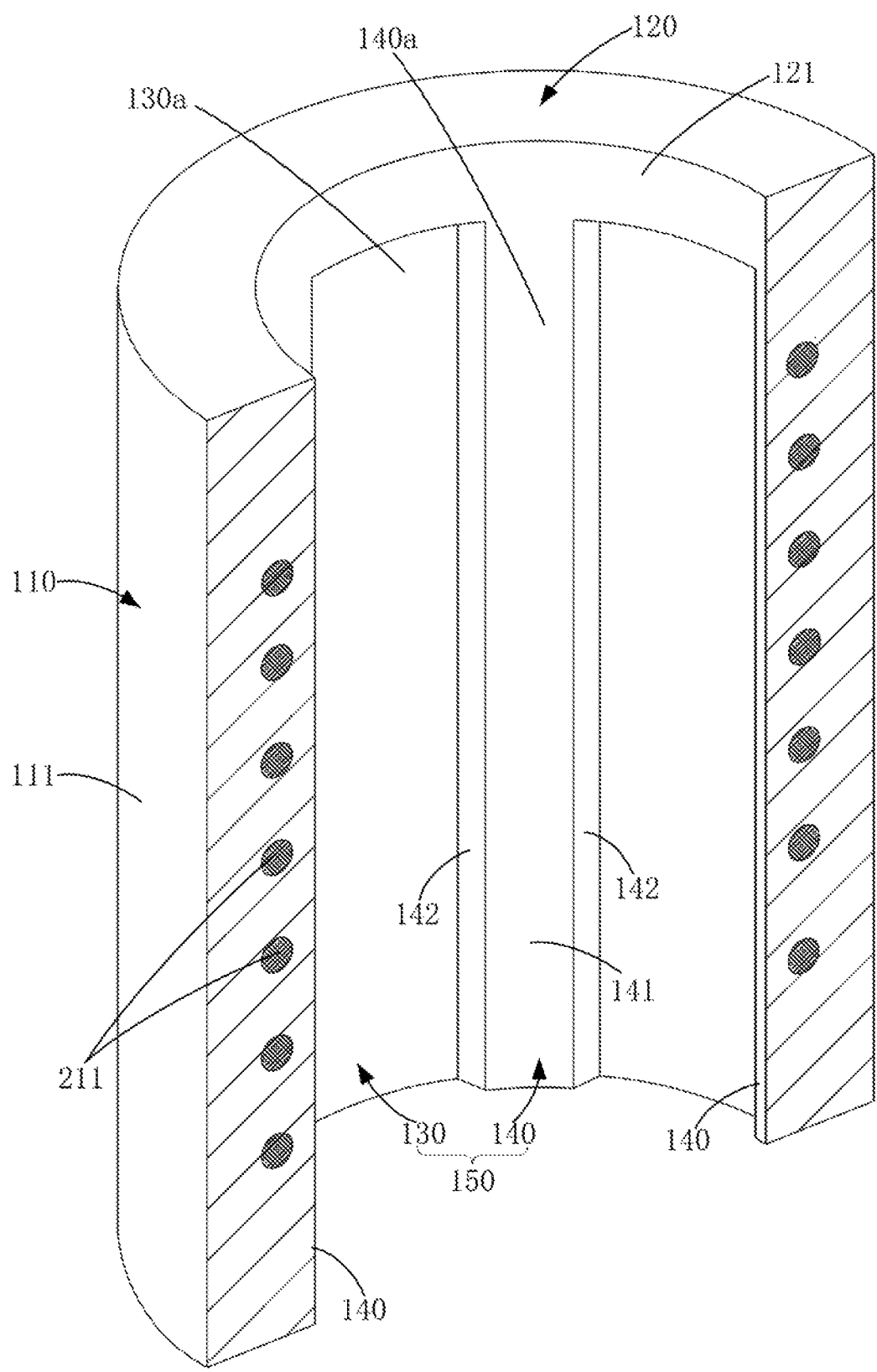
FIG. 5 is a perspective cut-away view corresponding to FIG. 4.
Figure 6:
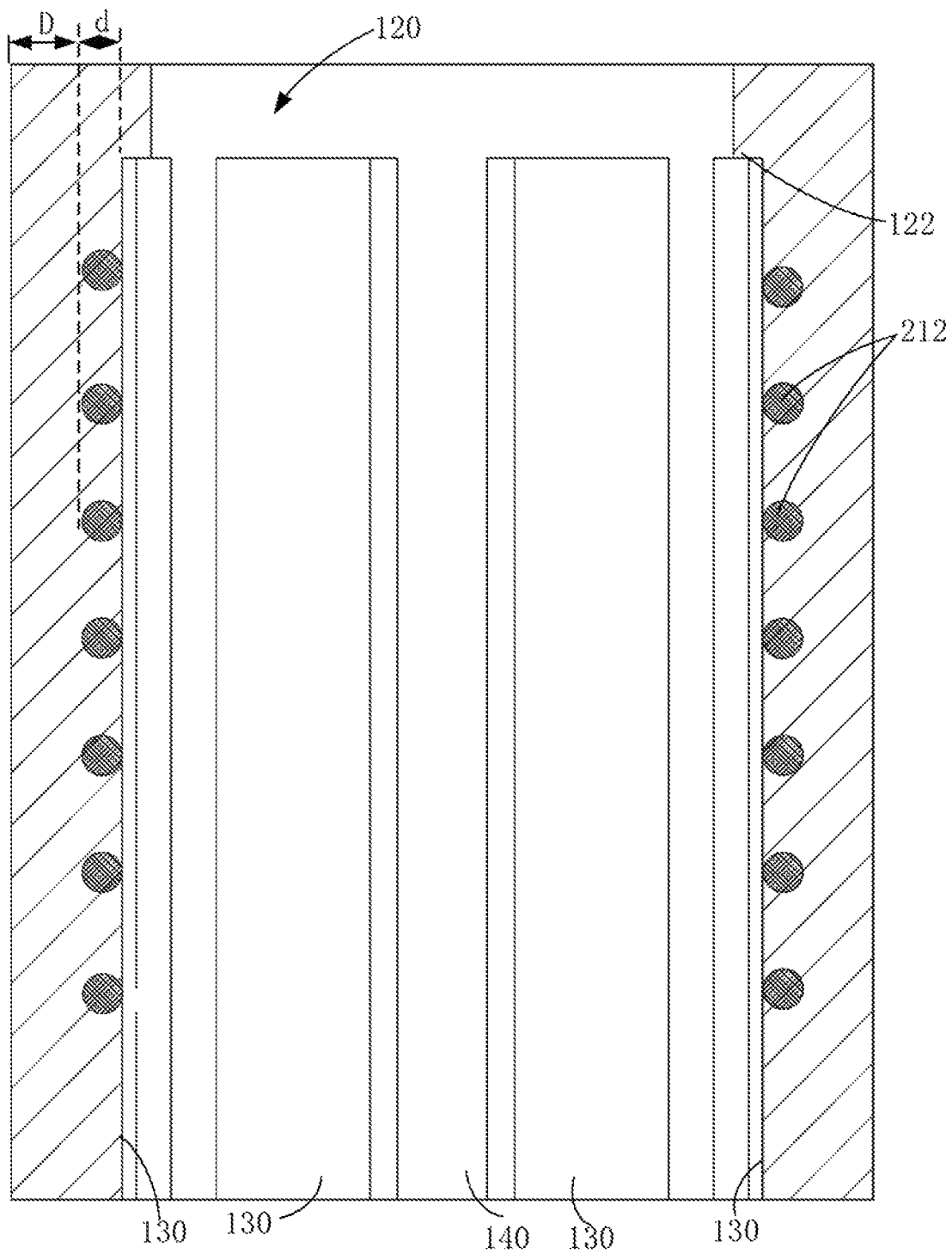
FIG. 6 is a cross-sectional view along the line F-F of FIG. 3.
Figure 7:
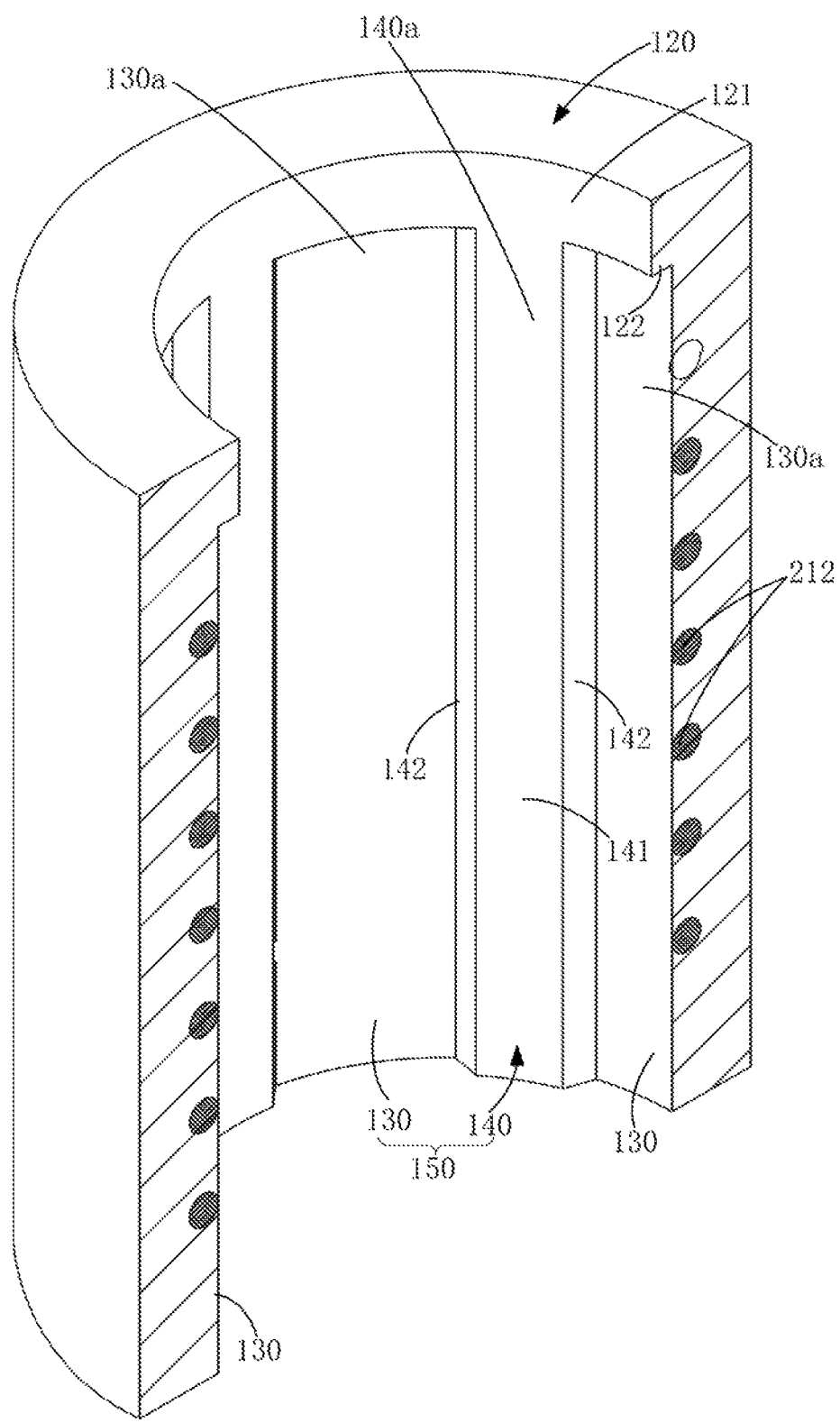
FIG. 7 is a perspective sectional view corresponding to FIG. 6.
Figure 10:
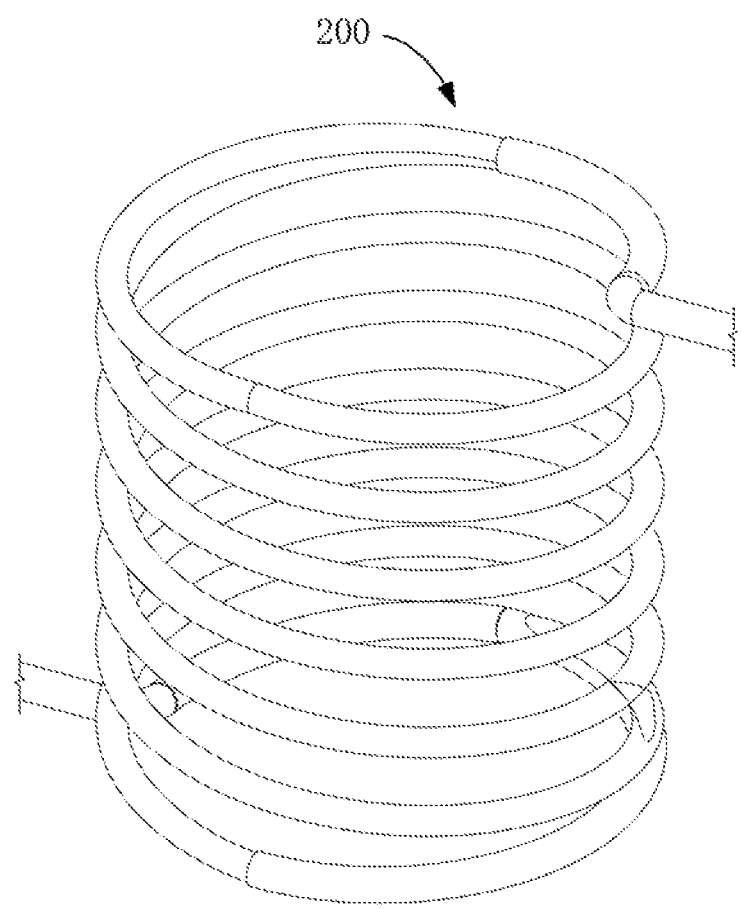
FIG. 10 is a perspective view of a heating unit of FIG. 1.

Referring to FIGS. 1, 2 and 10, an atomizing assembly 10 according to an embodiment includes a liquid absorbing unit 100 and a heating unit 200. The liquid absorbing unit 100 is used for absorbing and storing liquid. The heating unit 200 is a spiral-shaped heating wire 210, and a diameter of the heating wire 210 can be, e.g., 0.1 mm to 0.5 mm. The heating wire 210 can atomize the liquid stored in the liquid absorbing unit 100 to generate smoke.

Referring to FIGS. 1, 2, 5 and 7, the liquid absorbing unit 100 includes a hollow cylindrical tube 110 having a substantially cylindrical outer surface 111. The liquid absorbing unit 100 is provided with an atomizing channel 12 in a middle portion in an axis direction of the liquid absorbing unit 100. The liquid absorbing unit 100 has an atomizing surface 150, which is a sidewall of the atomizing channel 12. In other words, the atomizing surface 150 defines a boundary of the atomizing channel 12 through which the smoke flows. Alternatively, the liquid absorbing unit 100 may have other shapes, such as a prism or other polygons.

The heating wire 210 includes a plurality of embedded portions 212 and a plurality of buried portions 211, which are alternatively arranged (it means that the embedded portions 212 and the buried portions are arranged in interval). The embedded portion 212 is embedded in the liquid absorbing unit 100. A part of edge of the embedded portion 212 is internally tangent to the corresponding atomizing surface 150. In other words, in a radial direction of the atomizing channel 12, distance between an edge of the embedded portion 212 and its corresponding atomizing surface 150 is zero. Theoretically, a tangent between the atomizing surface 150 and the embedded portion 212 is not completely covered by the atomizing surface 150, and the tangent of the embedded portion 212 is visible to naked eyes, while the rest of the embedded portion 212 is completely hidden in the liquid absorbing unit 100 and is not visible to the naked eyes. The buried portion 211 is completely wrapped by and hidden in the liquid absorbing unit 100. In the radial direction of the atomizing channel 12, a predetermined distance (greater than zero) is designed between an edge of the buried portion 211 and its corresponding atomizing surface 150, thereby enabling the entire buried portion 211 to be completely invisible to the naked eyes.

Figure 8:
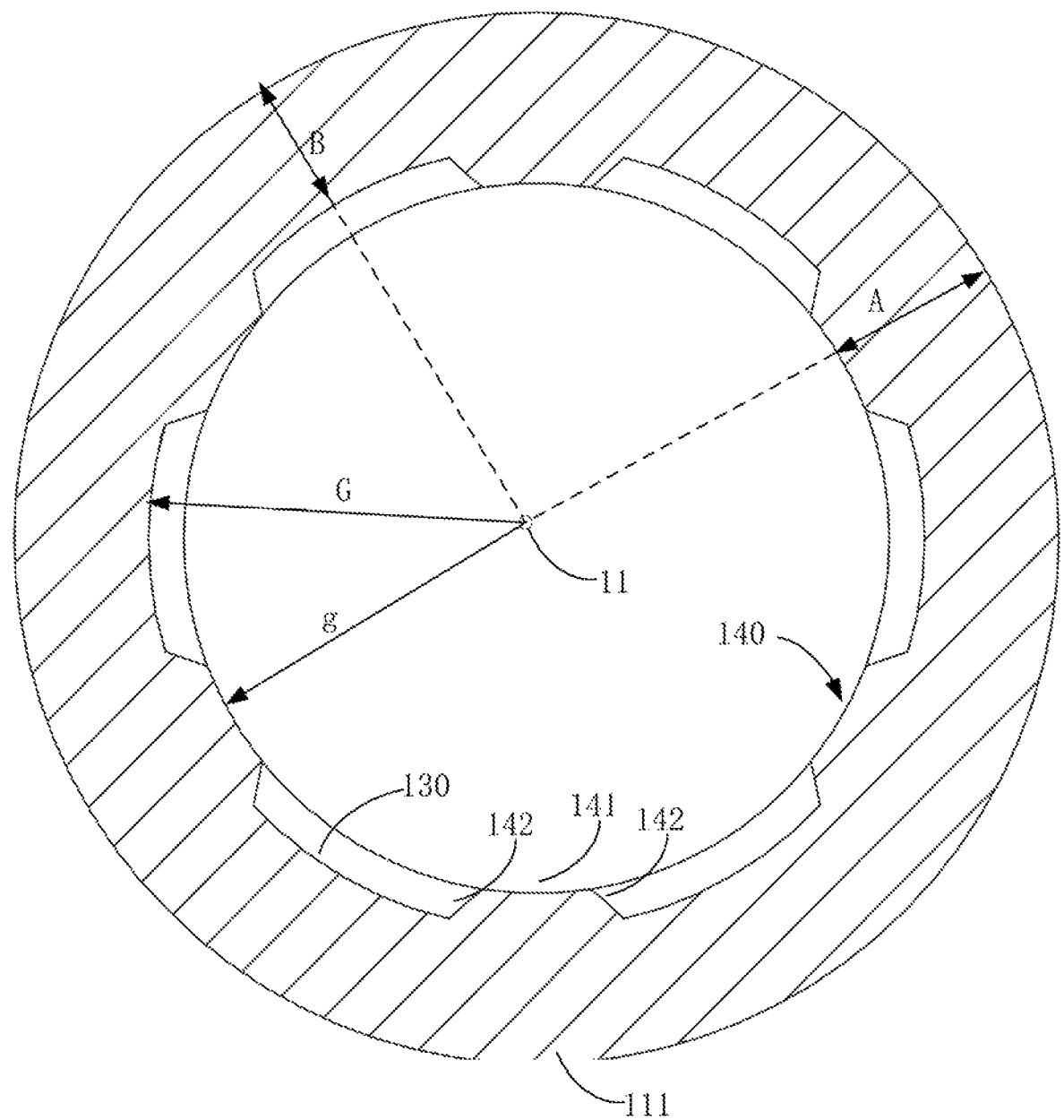
FIG. 8 is a cross-sectional view of the atomizing assembly of FIG. 1.
Figure 9:
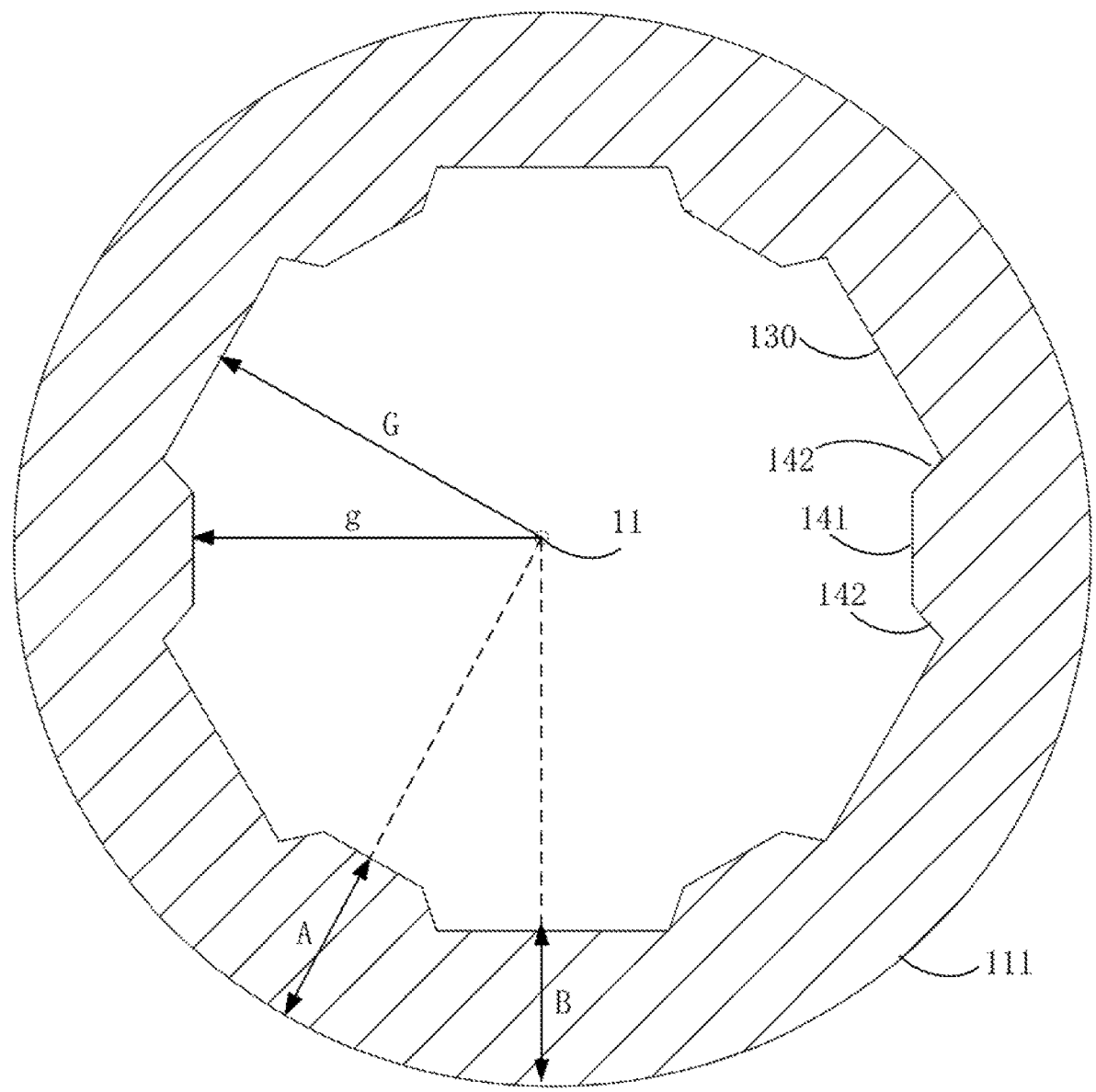
FIG. 9 is a cross-sectional view of the atomizing assembly according to another embodiment.

Referring to FIGS. 1 and 2, the atomizing surface 150 includes a plurality of concave unit surfaces 130 and a plurality of convex unit surfaces 140. Each of the concave unit surface 130 and the convex unit surface 140 extends in the axial direction of the cylindrical tube 110. The plurality of concave unit surfaces 130 is arranged spaced apart in a circumferential direction of the atomizing channel 12, and both ends of each convex unit surface 140 are respectively connected to two adjacent concave unit surfaces 130. Referring to FIGS. 8 and 9, the hollow cylindrical tube 110 has a central axis 11, and a radial distance G from the concave unit surface 130 to the central axis 11 is greater than a radial distance g from the convex unit surface 140 to the central axis 11. In other words, referring to FIGS. 3 to 7, the convex unit surface 140 can be regarded as a surface of a convex strip 140a disposed in the hollow cylindrical tube 110, and the concave unit surface 130 can be regarded as a bottom surface of a groove 130a located between two adjacent convex strips 140a. In a radial direction of the hollow cylindrical tube 110, the surface of the convex strip 140a is closer to the central axis 11 than the bottom surface of the groove 130a. The embedded portion 212 corresponds to the groove 130a, and the edge of the embedded portion 212 is internally tangent to the concave unit surface 130. The buried portion 211 corresponds to the convex strip 140a, and a predetermined distance is designed between the edge of the buried portion 211 and the convex unit surface 140. In other words, the buried portion 211 is completely covered and hidden by the convex strip 140a in the hollow cylindrical tube 110.

Referring to FIGS. 8 and 9, in some embodiments, the concave unit surface 130 is an arc surface that bends toward the central axis 11 of the hollow cylindrical tube 110. The convex unit surface 140 includes a first surface 141 and two second surfaces 142, a radial distance from the first surface 141 to the central axis 11 is less than a radial distance from the second surface 142 to the central axis 11. The first surface 141 is closer to the central axis 11 than the second surface 142 in the radial direction of the hollow cylindrical tube 110. One of the second surfaces 142 is connected between an end of the first surface 141 and one of the convex unit surfaces 130, and the other of the second surfaces 142 is connected between the other end of the first surface 141 and the other convex unit surfaces 130. The first surface 141 is the arc surface which is also bended toward the central axis 11 of the hollow cylindrical tube 110. The second surface 142 is a flat surface, and a tangent plane of the first surface 141 is formed at a junction between the first surface 141 and the second surface 142. The two second surfaces 142 respectively form a same angle with the tangent plane. In other embodiments, the convex unit surface 130, the first surface 141, and the second surface 142 can all be the flat surface or other shapes with curved surfaces or the like.

A radial distance from the first surface 141 to an outer surface 111 of the hollow cylindrical tube 110 is A, where 0.9 mm≤A≤1.1 mm. For example, A may be values of 0.9 mm, 1 mm or 1.1 mm or the like, such that maximum thickness of tube wall of the hollow cylindrical tube 110 is reasonably selected to ensure that the hollow cylindrical tube 110 has sufficient mechanical strength. The radial distance from the concave unit surface 130 to the outer surface 111 of the hollow cylindrical tube 110 is B, where 0.7 mm≤B≤0.9 mm. For example, B may be values of 0.7 mm, 0.8 mm or 0.9 mm or the like. In consideration of the diameter of the heating wire 210, it should be ensured to keep a reasonable space between the edge of the embedded portion 212 and the outer surface 111 of the hollow cylindrical tube 110 and prevent excessive heat on the embedded portion 212 from being conducted to the outer surface 111 of the hollow cylindrical tube 110, thereby preventing a user from having uncomfortable experience that the hands are burnt.

The aforementioned atomizing assembly 10 has at least three advantages. First, the buried portion 211 is completely buried in the hollow cylindrical tube 110, the hollow cylindrical tube 110 completely wraps the entire buried portion 211, thus further fixing the buried portion 211, such that the hollow cylindrical tube 110 can effectively support and protect the buried portion 211, and the heating wire 210 is effectively prevented from falling off the hollow cylindrical tube 110. Second, since the buried portion 211 is completely wrapped by the hollow cylindrical tube 110, more liquid will be attached to the surface of the buried portion 211 compared with the embedded portion 212. When the entire heating wire 210 is energized, heat generated by unit length buried portion 211 is less than heat generated by unit length embedded portion 212 in a given time, and total amount of the liquid heated by the unit length buried portion 211 is greater than the total amount of the liquid heated by the unit length embedded portion 212. Therefore, operating temperature of the buried portion 211 is lower than operating temperature of the embedded portion 212, and an atomizing temperature of the liquid corresponding to the buried portion 211 is lower than that corresponding to the embedded portion 212. The smoke atomized by the buried portion 211 is volatilized from the convex unit surface 140 to the atomizing channel 12, the smoke atomized by the embedded portion 212 volatilizes from the concave unit surface 130 to the atomizing channel 12. Tastes of two types of the smoke will be different, in other words, the liquid is atomized at different temperatures, and finally diversified tastes atomized by the atomizing assembly 10 is achieved. Third, when the heating wire 210 is energized, the embedding portion 212 is heated faster than the buried portion 211 due to more liquid will be attached to a surface of the buried portion 211. The embedding portion 212 first reaches initial atomizing temperature at which the liquid is atomized into the smoke, such that the embedding portion 212 atomizes the liquid in a short time, thus ensuring a rapid formation of the smoke by the atomizing assembly 10.

Of course, both surfaces of the embedded portion 212 and the buried portion 211 of the heating wire 210 are in direct contact with the liquid, and surface temperature of the entire heating wire 210 is uniformly distributed, thereby preventing the liquid from bursting due to local excessive temperature of the heating wire 210. It is also avoided that the liquid generates a cracking reaction at a position where temperature of the heating wire 210 is too high to form a toxic gas such as formaldehyde.

In some embodiments, the hollow cylindrical tube 110 is made of a porous ceramic material. The outer surface 11 of the hollow cylindrical tube 110 is in direct contact with the liquid in a liquid storage unit (not shown) to absorb the liquid in the liquid storage unit. The liquid in the liquid storage unit is uniformly distributed on the inner and outer surfaces of the porous ceramic material under capillary effect through the outer surface 111. The porosity of the porous ceramic material is 30% to 60%, the optimal value is 35% to 45%. If the porosity is too high, the risk of leakage will be increased; if the porosity is too low, there will be insufficient liquid supply and other issues.

Referring to FIGS. 4 to 7, in some embodiments, a radial distance D from the heating wire 210 to the outer surface 111 of the hollow cylindrical tube 110 is greater than the radial distance d from the heating wire 210 to the atomizing surface 150. When the heating wires 210 heats and atomizes the liquid, temperature of the outer surface 11I of the liquid absorbing unit 100 is lower than the atomizing surface 150 due to difference in heat loss during heat conduct for the distance difference, thereby ensuring that most of heat generated by the heating wire 210 is used to atomize the liquid and avoiding that excessive heat is conducted to the outer surface 111 resulting in a temperature increase of the non-atomized liquid in the liquid storage unit. A phenomenon that the hands are burnt during use is prevented, while utilization rate of energy of the heating wire 210 is improved.

In other embodiments, for example, a thermal conductivity of the hollow cylindrical tube 110 can radially decrease from inside to outside. As another example, referring to FIG. 4, the hollow cylindrical tube 110 includes an inner body 113 and an outer body 112 connected to each other. The inner body 113 is disposed adjacent to the atomizing channel 12, and the atomizing surface 150 is located on the inner body 113. The outer body 112 is disposed away from the atomizing channel 12, and the outer surface 111 is located on the outer body 112. The thermal conductivity of the inner layer 113 is greater than the thermal conductivity of the outer layer 112, and the heating wire 210 is embedded or buried in the inner layer 113. The higher the thermal conductivity is, the stronger the thermal conductivity is, in other words, the more heat is conducted per unit time. When the heating wire 210 is energized, the amount of heat distributed on the atomizing surface 150 is greater than the outer surface 111 of the hollow cylindrical tube 110, so that the above two designs can also avoid the uncomfortable experience that the hands are burnt and improve an energy utilization ratio.

Referring to FIGS. 2 and 10, in some embodiments, radial distances of both the buried portion 211 and the embedded portion 212 to the central axis 11 are equal. In other words, using a flat surface perpendicular to the central axis 11 as a reference plane, orthographic projections of both the buried portion 211 and the embedded portion 212 on the reference plane are located on the same circle, and the central axis 11 passes through the center of the circle, thereby facilitating the manufacture and installation of the entire heating wire 210.

Referring to FIGS. 1 and 2, and FIGS. 5 to 7, in some embodiments, the liquid absorbing unit 100 further includes at least one liquid blocking tube 120 coaxially arranged with the hollow cylindrical tube 110, in other words, the central axes 11 thereof coincide with each other. The liquid blocking tube 120 is located at one end of the hollow cylindrical tube 110. A radial distance from an inner surface 122 of the liquid blocking tube 120 to the central axis 11 of the hollow cylindrical tube 110 is less than or equal to the minimum radial distance from the atomizing surface 150 to the central axis 11, such that a partial end face 122 of the liquid blocking tube 120 is connected between the concave unit surface 130 and the inner surface 121 of the liquid blocking tube 120. The partial end face 122 of the liquid blocking tube 120 extends in the radial direction of the hollow cylindrical tube 110 and forms just a step surface. In general, convex unit surface 140 can be regarded as the surface of the convex strip 140a disposed in the hollow cylindrical tube 110, the concave unit surface 130 can be regarded as the bottom surface of the groove 130a located between two adjacent convex strips 140a. The groove 130a extends in the axial direction of the hollow cylindrical tube 110 and stops at the step surface, and the groove 130a does not extend to the inner surface 121 of the liquid blocking tube 120. Therefore, by providing the liquid blocking tube 120, it is possible to prevent the liquid in the hollow cylindrical tube 110 from being sucked out during smoking of the user. In other embodiments, two liquid blocking tubes 120 are connected to both ends of the hollow cylindrical tube 110, respectively.

An electronic cigarette including the above-described atomizing assembly 10 is also provided, such that the electronic cigarette has the advantages of diversified tastes and rapid smoke generation.

Figure 11:
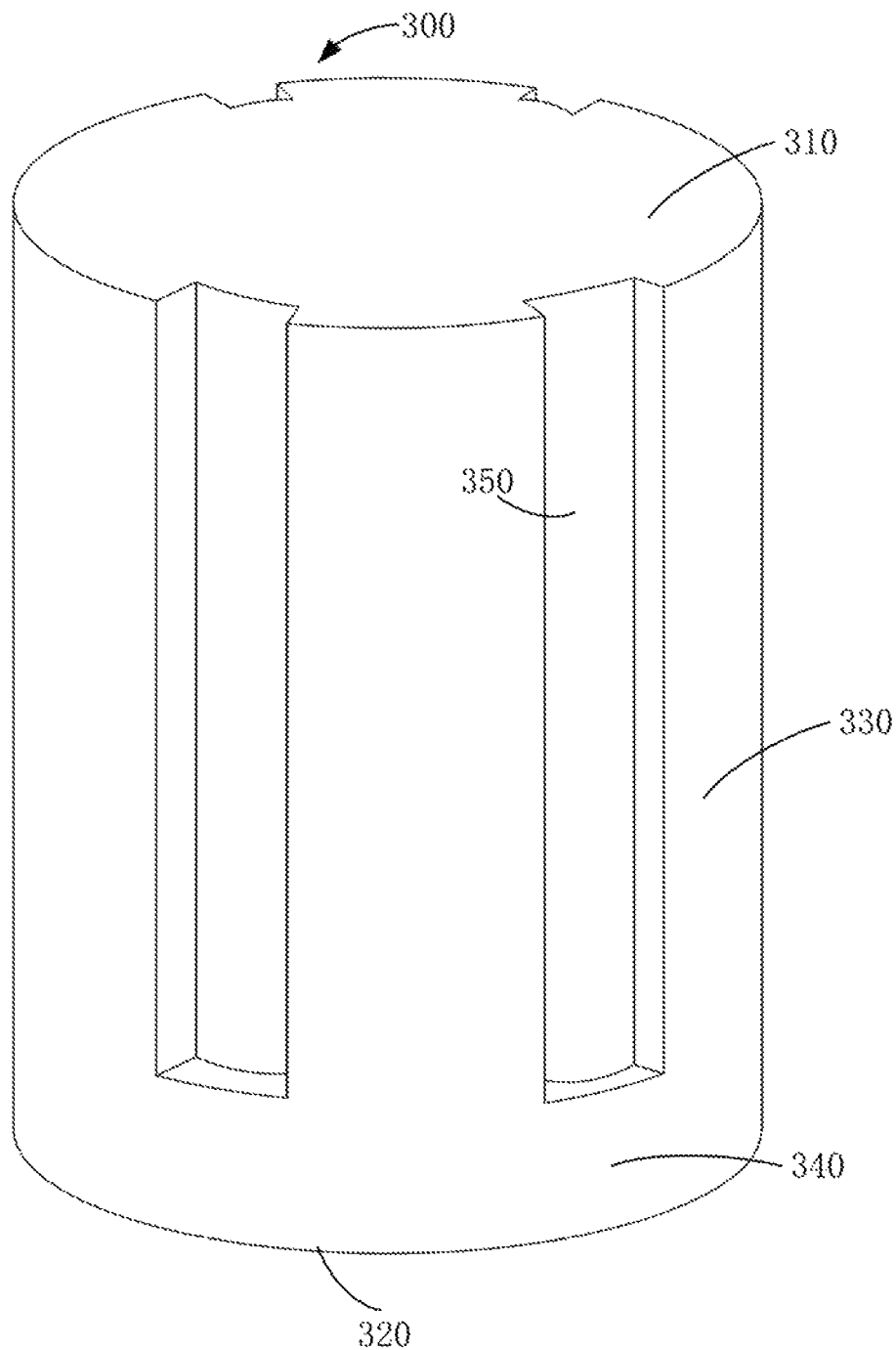
FIG. 11 is a perspective view of a fixing post according to an embodiment.
Figure 12:
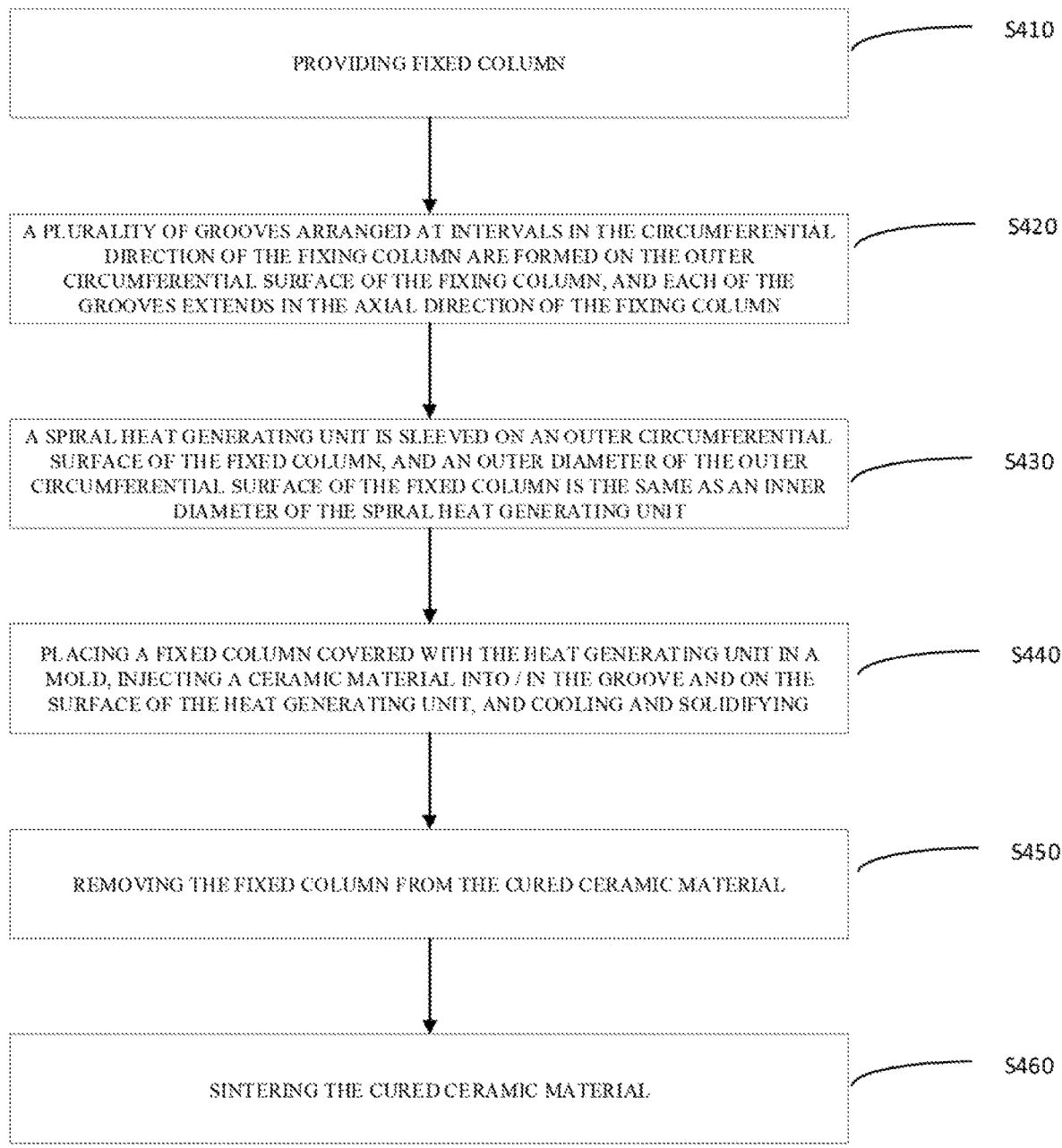
FIG. 12 is a flow chart of a method of manufacturing the atomizing assembly according to an embodiment.

Referring to FIGS. 11 and 12, the present disclosure further provides a method of manufacturing the atomizing assembly. The method mainly includes the following steps of:

In step S410, a fixing post 300 is provided.

In step S420, a plurality of grooves 350 are defined on an outer circumferential surface of the fixing post 300. The plurality of grooves 350 are spaced apart and extend in an axial direction of the fixing post 300.

In step S430, a spiral-shaped heating unit 200 is sleeved on the outer circumferential surface of the fixing post 300. The outer diameter of the fixing post 300 is the same as an inner diameter of the spiral-shaped heating unit 200, such that the spiral-shaped heating unit 200 abuts against the outer circumferential surface of the fixing post 300. A predetermined distance is designed between the spiral-shaped heating unit 200 and a bottom surface of the groove 350 in a radial direction of the fixing post 300.

In step S440, the fixing post 300 sleeved with the heating unit 200 is placed into a cavity of a mold, and molten ceramic material is injected into the cavity of the mold. The ceramic material liquid fills the groove 350 and covers a surface of the heating unit 200. The liquid ceramic material is then solidified by cooling to form a solid ceramic material.

In step S450, the fixing post 300 is removed from the solidified ceramic material.

In step S460, the solidified ceramic material is sintered.

Through the above-described steps, the liquid absorbing unit 100 is finally formed from the ceramic material. A part of the heating unit 200 (i.e., the embedded portion 212) is embedded in the liquid absorbing unit 100 and an edge of the heating unit 200 is internally tangent to the inner surface of the liquid absorbing unit 100. The other part of the heating unit 200 (i.e., the buried portion 211) is wrapped by and hidden in the liquid absorbing unit 100.

In some embodiments, in step S420, the groove 350 extends to only an end face 310 of the fixing post 300, a predetermined distance is designed between an end face of the groove 350 and the other end face 320 of the fixing post 300, which facilitates removal of the fixing post 300 from the solidified ceramic material. A portion 330 of the fixing post 300 with the groove 350 forms the hollow cylindrical tube 110 of the liquid absorbing unit 100. A portion 340 of the fixing post 300 without the groove 350 forms the liquid blocking tube 120 of the liquid absorbing unit 100. In other embodiments, for example, when the groove 350 extends to the upper and lower end faces 310, 320 of the fixing post 300, the formed liquid absorbing unit 100 includes only the hollow cylindrical tube 110, and does not include the liquid blocking tube 120. As another embodiment, when the groove 350 does not extend to any one of the end faces of the fixing post 300, the formed liquid absorbing unit 100 includes a hollow cylindrical tube 110 and two liquid blocking tubes 120, which are respectively provided at both ends of the hollow cylindrical tube 110. Of course, in order to facilitate the removal of the fixing post 300 from the solidified ceramic material, a mold ejection mechanism is provided in the mold. When the groove 350 extends to at most an end face of the fixing post 300, it is apparent that the axial extension length of the groove 350 on the fixing post 300 is less than the axial length of the fixing post 300 itself.

The fixing post 300 is a cylinder, and both the concave unit surface 130 and the first surface 141 on the liquid absorbing unit 100 are arc surfaces after the liquid absorbing unit is solidified. The fixing post 300 can also be a prism, such as a pentagonal prism or a hexagonal prism. Both the concave unit surface 130 and the first surface 141 on the liquid absorbing unit 100 is plane after the liquid absorbing unit is solidified.

After step S460, the method may further include: injecting and solidifying a second ceramic material on a surface of the first ceramic material, the second ceramic material has a lower thermal conductivity than the first ceramic material.

Figure 13:
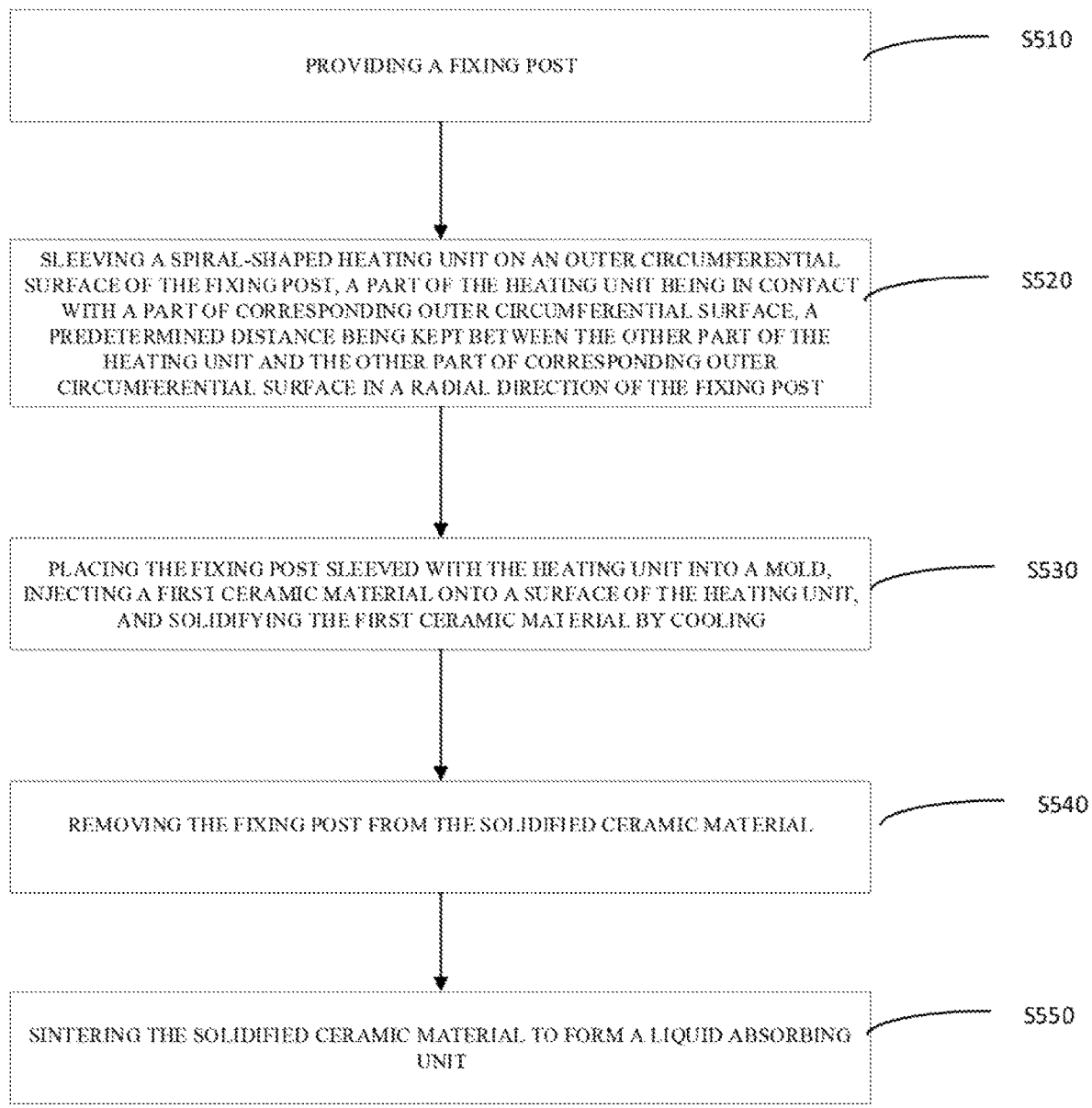
FIG. 13 is a flow chart of a method of manufacturing the atomizing assembly according to another embodiment.

Referring to FIG. 13, the present disclosure further provides a method of manufacturing the atomizing assembly. The method mainly includes the following steps of:

In step S510, a fixing post 300 is provided.

In step S520, a spiral-shaped heating unit 200 is sleeved on an outer circumferential surface of the fixing post 300, a part of the heating unit 200 is in contact with a part of corresponding outer circumferential surface, a predetermined distance is designed between the other part of the heating unit 200 and the other part of corresponding outer circumferential surface in a radial direction of the fixing post 300.

In step S530, the fixing post 300 sleeved with the heating unit 200 is placed into a mold, a first ceramic material is injected onto a surface of the heating unit 200, and the first ceramic material is solidified by cooling.

In step S540, the fixing post 300 from the solidified ceramic material is removed.

In step S550, the solidified ceramic material is sintered to form a liquid absorbing unit.

The main difference between the above-mentioned two embodiments of the method of manufacturing the atomizing assembly is that, the outer circumferential surface of the fixing post 300 is not provided with the groove 350. During the sleeving process of the spiral-shaped heating unit 200, a part of the heating unit 200 abuts against the corresponding outer circumferential surface of the fixing post 300. Meanwhile, in the radial direction of the fixing post 300, a predetermined distance is designed between another part of the heating unit 200 and the corresponding outer circumferential surface of the fixing post 300. In other words, the other part of the heating unit 200 is not in contact with the outer circumferential surface of the fixing post 300. After the fixing post 300 sleeved with the heating unit 200 is placed into a mold to inject a ceramic material, the ceramic material is solidified and sintered to form the liquid absorbing unit 100. At this time, the part of the heating unit 200 abutting against the outer circumferential surface of the fixing post 200 forms the embedded portion 212, and the other part of the heating unit 200 is not in contact with the outer circumferential surface of the fixing post 200 forms the buried portion 211.

The various technical features of the above-described embodiments can be arbitrarily combined. For the sake of brevity of description, all possible combinations of the respective technical features in the above-described embodiments have not been described, however, as long as there is no contradiction in the combination of these technical features, it should be deemed to be the scope of the specification.

The above-described embodiments represent only several embodiments of the disclosure. The description of the embodiments is more specific and detailed, but are not therefore to be construed as limiting the scope of the disclosure patent. It should be noted that several modifications and improvements can be made to those of ordinary skill in the art without departing from the inventive concept, all of the modifications and improvements fall within the scope of the disclosure. Therefore, the scope of protection of the disclosure patent shall be subject to the appended claims.

What is claimed is:

1. An atomizing assembly, comprising:
    a liquid absorbing unit configured to absorb and store liquid, the liquid absorbing unit forming an atomizing channel therein and comprising an atomizing surface on which the liquid is atomized and volatilized, and the atomizing surface defining a boundary of the atomizing channel; and
    a heating unit configured to atomize the liquid, the heating unit comprising a buried portion and an embedded portion connected to each other, the embedded portion being embedded in the liquid absorbing unit and being internally tangent to the corresponding atomizing surface, the buried portion being wrapped in the liquid absorbing unit, wherein a predetermined distance is designed between the buried portion and the corresponding atomizing surface in a radial direction of the atomizing channel.

2. The atomizing assembly of claim 1, wherein the liquid absorbing unit comprises a hollow cylindrical tube, the atomizing channel extending in an axis direction of the liquid absorbing unit.

3. The atomizing assembly of claim 2, wherein the heating unit is a spiral-shaped heating wire, a plurality of buried portions and a plurality of embedded portions being alternatively arranged.

4. The atomizing assembly of claim 2, wherein the atomizing surface comprises a plurality of concave unit surfaces and a plurality of convex unit surfaces, the concave unit surfaces being arranged spaced apart in a circumferential direction of the atomizing channel, each convex unit surface being connected to two adjacent concave unit surfaces, a radial distance from the concave unit surface to a central axis of the hollow cylindrical tube being greater than a radial distance from the convex unit surface to the central axis, an edge of the embedded portion being internally tangent to the concave unit surface, wherein the predetermined distance is designed between an edge of the buried portion and the convex unit surface.

5. The atomizing assembly of claim 4, wherein the concave unit surface is a flat surface or an arc surface.

6. The atomizing assembly of claim 4, wherein the convex unit surface comprises a first surface and two second surfaces, a radial distance from the first surface to the central axis is less than a radial distance from the second surface to the central axis, the second surface is connected between the first surface and the convex unit surface.

7. The atomizing assembly of claim 6, wherein the first surface is a flat surface or an arc surface, and the second surface is a flat surface.

8. The atomizing assembly of claim 6, wherein a radial distance from the first surface to an outer surface of the hollow cylindrical tube is A, 0.9 mm≤A≤1.1 mm.

9. The atomizing assembly of claim 4, wherein the radial distance from the concave unit surface to the outer surface of the hollow cylindrical tube is B, 0.7 mm≤B≤0.9 mm.

10. The atomizing assembly of claim 2, wherein radial distances of both the buried portion and the embedded portion to a central axis of the hollow cylindrical tube are equal.

11. The atomizing assembly of claim 2, wherein the liquid absorbing unit further comprises a liquid blocking tube coaxially arranged at an end of the hollow cylindrical tube, a radial distance from an inner surface of the liquid blocking tube to a central axis of the hollow cylindrical tube being less than or equal to the minimum radial distance from the atomizing surface to the central axis.

12. An electronic cigarette, comprising an atomizing assembly of claim 1.

13. A method of manufacturing an atomizing assembly, comprising:
    providing a fixing post;
    defining a plurality of grooves circumferentially spaced apart on an outer circumferential surface of the fixing post, each groove extending in an axial direction of the fixing post;
    sleeving a spiral-shaped heating unit on the outer circumferential surface of the fixing post, an outer diameter of the fixing post being the same as an inner diameter of the spiral-shaped heating unit;
    placing the fixing post sleeved with the heating unit into a mold, injecting a first ceramic material into the grooves and onto a surface of the heating unit, and solidifying the first ceramic material by cooling;
    removing the fixing post from the solidified ceramic material; and
    sintering the solidified ceramic material to form a liquid absorbing unit;
    wherein a part of the heating unit is embedded in the liquid absorbing unit and an edge of the heating unit is internally tangent to an inner surface of the liquid absorbing unit, and the other part of the heating unit being wrapped in the liquid absorbing unit.

14. The method of claim 13, wherein the grooves extend to an end face of the fixing post, and a predetermined distance is designed between an end face of the groove and the other end face of the fixing post.

15. The method of claim 13, wherein a portion of the fixing post with the groove forms a hollow cylindrical tube of the liquid absorbing unit, a portion of the fixing post without the groove forming a liquid blocking tube of the liquid absorbing unit.

16. The method of claim 13, wherein the fix column is a cylinder, and both a concave unit surface and a first surface on the liquid absorbing unit being arc surfaces after the liquid absorbing unit is solidified.

17. The method of claim 13, wherein after injecting the first ceramic material into the grooves and onto the surface of the heating unit, and solidifying the first ceramic material by cooling, the method further comprises injecting and solidifying a second ceramic material on a surface of the first ceramic material, the second ceramic material having a lower thermal conductivity than the first ceramic material.

18. A method of manufacturing an atomizing assembly, comprising:

providing a fixing post;

sleeving a spiral-shaped heating unit on an outer circumferential surface of the fixing post, a part of the heating unit being in contact with a part of corresponding outer circumferential surface, a predetermined distance being designed between the other part of the heating unit and the other part of corresponding outer circumferential surface in a radial direction of the fixing post;

placing the fixing post sleeved with the heating unit into a mold, injecting a first ceramic material onto a surface of the heating unit, and solidifying the first ceramic material by cooling;

removing the fixing post from the solidified ceramic material; and sintering the solidified ceramic material to form a liquid absorbing unit;

wherein a part of the heating unit is embedded in the liquid absorbing unit and an edge of the heating unit is internally tangent to an inner surface of the liquid absorbing unit, and the other part of the heating unit being wrapped in the liquid absorbing unit.

\* \* \* \* \*